(12) United States Patent
Wegerer et al.

(10) Patent No.: US 7,795,479 B1
(45) Date of Patent: Sep. 14, 2010

(54) TEMPERATURE CONTROLLED ADSORPTION MULTI-STEP REGENERATION CYCLE

(75) Inventors: David A. Wegerer, Lisle, IL (US); Stephen R. Dunne, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/637,829

(22) Filed: Dec. 15, 2009

(51) Int. Cl.
*C07C 29/76* (2006.01)

(52) U.S. Cl. .................. 568/916; 568/903; 568/913

(58) Field of Classification Search .......... 568/869, 568/916, 913, 903
See application file for complete search history.

(56) References Cited

U.S. PATENT DOCUMENTS

| | | | |
|---|---|---|---|
| 4,297,172 A * | 10/1981 | Kyle .................. | 203/19 |
| 4,418,545 A | 12/1983 | Markfort | |
| 4,451,270 A | 5/1984 | Roman | |
| 4,479,814 A | 10/1984 | Oliker | |
| 4,594,856 A | 6/1986 | Rothmeyer | |
| 4,846,135 A | 7/1989 | Tiphaine | |
| RE33,352 E | 9/1990 | Roman et al. | |
| 5,116,510 A | 5/1992 | Sircar et al. | |
| 5,571,477 A | 11/1996 | Nagy et al. | |
| 5,768,904 A | 6/1998 | Tagamolila et al. | |
| 5,802,870 A | 9/1998 | Arnold et al. | |
| 5,823,003 A | 10/1998 | Rosser, Jr. et al. | |
| 5,845,507 A | 12/1998 | Critoph et al. | |
| 5,953,927 A | 9/1999 | Tagamolila et al. | |
| 6,372,026 B1 | 4/2002 | Takemasa et al. | |
| 6,423,275 B1 | 7/2002 | D'Souza | |
| 6,591,630 B2 | 7/2003 | Smith et al. | |
| 6,601,404 B1 | 8/2003 | Roderick | |
| 6,607,583 B2 | 8/2003 | Cowles et al. | |
| 7,422,993 B2 | 9/2008 | Takewaki et al. | |
| 7,497,089 B2 | 3/2009 | Kakiuchi et al. | |
| 7,578,143 B2 | 8/2009 | Critoph et al. | |
| 2005/0006310 A1 | 1/2005 | Agrawal et al. | |
| 2007/0000769 A1 | 1/2007 | Brown | |
| 2007/0238906 A1 | 10/2007 | Brown et al. | |
| 2008/0023181 A1 | 1/2008 | Dunne et al. | |
| 2008/0034785 A1 | 2/2008 | Yanagi | |
| 2008/0039665 A1 | 2/2008 | Brown et al. | |
| 2008/0176303 A1* | 7/2008 | Massie .................. | 435/163 |
| 2008/0245653 A1 | 10/2008 | Zhong et al. | |
| 2009/0025403 A1 | 1/2009 | Kakiuchi et al. | |

FOREIGN PATENT DOCUMENTS

| | | |
|---|---|---|
| DE | 3501216 A1 | 7/1996 |
| DE | 3702190 A1 | 8/1998 |
| EP | 0373538 A1 | 6/1990 |
| EP | 0394947 A2 | 10/1990 |
| EP | 1873462 A1 | 1/2008 |
| FR | 2619106 A1 | 2/1989 |
| FR | 2669087 A1 | 5/1992 |
| JP | 60129116 | 7/1985 |
| WO | WO 95/30469 A1 | 11/1995 |
| WO | WO 03/008091 A1 | 1/2003 |
| WO | WO 2008/155543 A2 | 12/2008 |
| WO | WO 2009/002893 A2 | 12/2008 |

OTHER PUBLICATIONS

U.S. Appl. No. 12/337,154 filed Dec. 17, 2008, Wegerer.
U.S. Appl. No. 12/337,248 filed Dec. 17, 2008, Dunne.
U.S. Appl. No. 12/555,445 filed Sep. 8, 2009, Dunne.
U.S. Appl. No. 12/555,450 filed Sep. 8, 2009, Wegerer.
"Adsorption of gas mixtures in TSA adsorbers under various heat removal conditions", Clausse, Chemical Engineering Science 59 (2004) 3657-3670.
"Internal heat and mass transfer during thermal desorption", Kuatbekov, chemical abstract, Teor Osn Khim Tekhnol 1973, vol. 7, No. 3, pp. 429-433.
"Isoconversional kinetic analysis of isothermal selective ethanol adsorption on zeolite type NaZSM-5", Adnadevic, Chem. Eng. Technol., 2007, 30, No. 9, 1228-1234.
"Isothermal composite adsorbent. Part I: Thermal characterisation", Meljac, Applied Thermal Engineering 27 (2007) 1009-1016.
"Production of cold heat energy by alcohol/activated carbon adsorption. . . ", Kanamori, Journal of Chemical Engineering of Japan, vol. 30, No. 3, 1997.
"TSA process with indirect heating and cooling: parametric analysis and scaling-up to practical sizes", Bonjour, Chemical Engineering and Processing 44 (2005) 969-977.

* cited by examiner

*Primary Examiner*—Elvis O Price
(74) *Attorney, Agent, or Firm*—Mark Goldberg

(57) ABSTRACT

Systems and processes for dehydration of a process stream in the production of motor fuel grade ethanol (MFGE) can include temperature controlled adsorption of water in the process stream, and heat pumping of the associated heat of adsorption. The process includes providing a process stream including ethanol and water to a first temperature controlled adsorber where water is removed by adsorption to produce a MFGE product stream and an associated heat of adsorption. A cooling fluid is provided to the first temperature controlled adsorber to remove heat of adsorption and produce a heated cooling fluid. Heat from the heated cooling fluid is provided to a heat sink. A multiple step regeneration cycle is provided that allows for increased recovery of MFGE product.

20 Claims, 5 Drawing Sheets

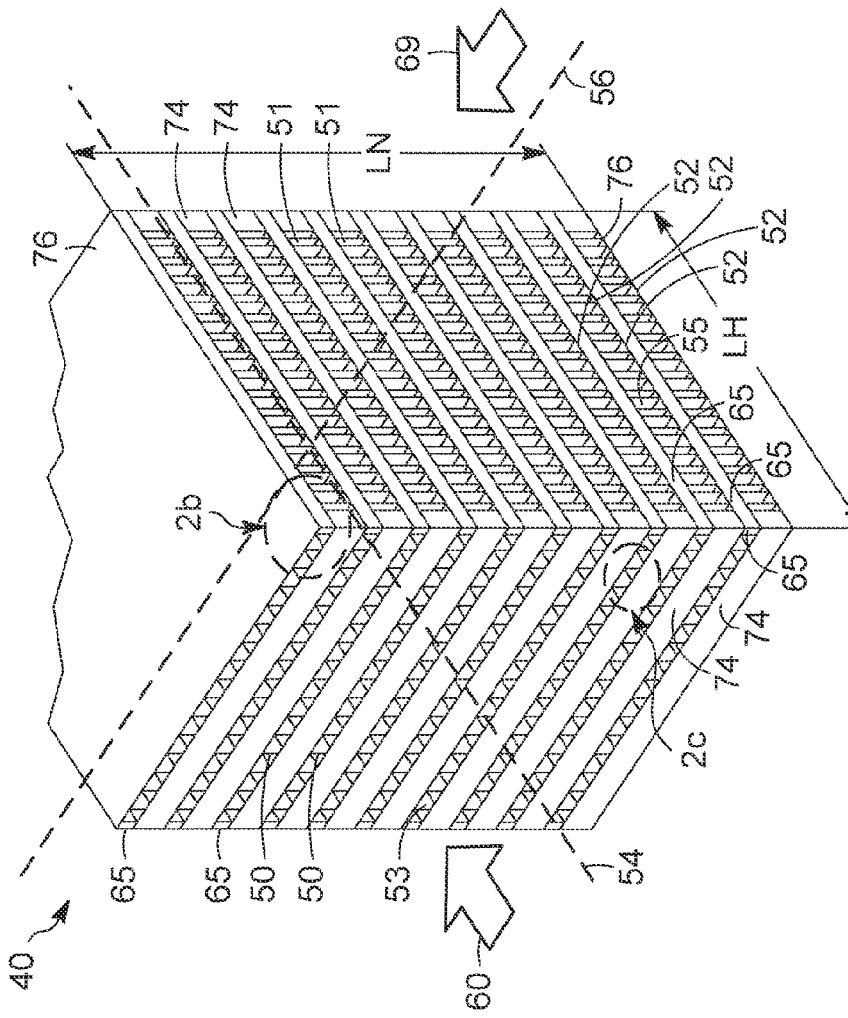
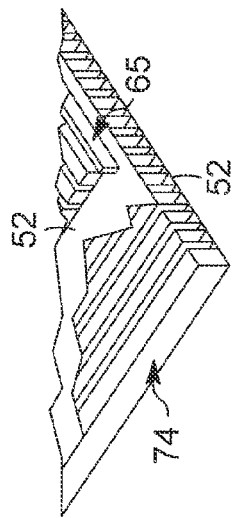
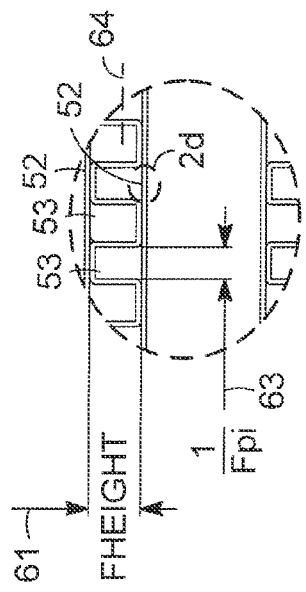
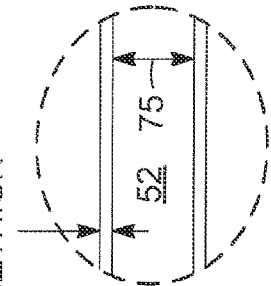

TEMPERATURE CONTROLLED ADSORPTION MULTI-STEP REGENERATION CYCLE

FIELD OF THE INVENTION

The systems and processes disclosed herein relate generally to the dehydration of fermentation effluent streams containing ethanol and water, such as fermentation beer. More particularly, systems and processes are disclosed herein relating to a multi-step regeneration cycle to be utilized in conjunction with temperature controlled adsorption of process streams for producing motor fuel grade ethanol (MFGE) in order to provide an increased recovery of MFGE.

DESCRIPTION OF RELATED ART

Adiabatic adsorption is a process that is employed for bulk water removal, within certain water concentration limits, and purification applications. For example, adiabatic adsorption via molecular sieves is a widely practiced method for removing water from process streams, such as, for example, the azeotropic mixture of ethanol and water exiting a rectifier column in the production of MFGE.

The adsorption and desorption reactions that occur during adiabatic adsorption are considered adiabatic since the adsorber and process fluid being treated constitute a system that does not exchange heat with any other adjacent stream within the adsorbent containing contactor. The dynamic nature of the adiabatic water adsorption process, specifically, temperatures rising during adsorption and falling during regeneration, necessarily reduces the adsorbent absolute and differential loading potentials, the latter due to less than perfect regeneration. Additionally, adiabatic operation of an adsorber results in a thermal front preceding the adsorption front. As a consequence, achievable product purities are lowered. For bulk water removal applications, this imposes an upper limit on the water concentration of the process fluid to be treated. The upper limit on water concentration results because in adiabatic adsorption systems, which do not have heat removal capability, the heat liberation associated with a high water content stream feeding an adiabatic adsorber can drive the product end of the bed to a sufficiently high temperature to reduce, or even eliminate, the driving force for adsorption.

As a result, processes for removing water from a mixture containing water and an organic compound to be dehydrated, such as, for example, ethanol, commonly involve process steps to remove water from the mixture prior to the mixture undergoing adsorption.

For example, motor fuel grade ethanol (MFGE) consumer product specifications typically limit water concentrations to less than 1% by volume, and in many countries less than 0.5% by volume. Fuel ethanol (E-95) quality for use in the USA is governed by the specifications listed in ASTM D 4806, entitled "Standard Specification for Denatured Fuel Ethanol for Blending with Gasolines for use as an Automotive Spark-Ignition Engine Fuel." The ASTM specification specifies a maximum water content of 1% by volume. However, due to the fact that ethanol is hygroscopic and easily picks up water from ambient air and the distribution system, the MFGE process specification for water content of the MFGE product is typically tighter than the ASTM specification, and, in at least some instances, can require a maximum water content of about 0.5% by weight. It should be noted that a product stream having about 99% by volume ethanol and about 1% by volume water has about 98.75% by weight ethanol and 1.25% by weight water.

Industrial processes for producing motor fuel grade ethanol (MFGE) include fermentation of sugars, including sugars derived from starches and lignocellulose. The effluent from the fermentation process, commonly known as fermentation beer, is a water-rich mixture containing water, alcohols, soluble solids, and insoluble solids. The alcohol content of fermentation beer is primarily ethanol. Beer from fermentation typically has very high water content, which can be in the range of about 70% by weight to about 90% percent by weight of the fermentation beer. The ethanol content of fermentation beer is dependent on the sugar source. For example, beer produced from fermenting sugars derived from corn starch can typically have an ethanol content in the range of about 5% to about 15% by weight, such as an ethanol content of about 10% by weight of the fermentation beer. Generally, the ethanol content of fermentation beer is in the range of from about 3% by weight to about 20% by weight. Accordingly, concentrating and purifying the ethanol contained in fermentation beer to achieve an MFGE product that meets specifications entails removing a relatively large amount of water.

Separating ethanol from beer is usually accomplished through distillation up to the ethanol-water azeotropic mixture concentration, which is about 95% by weight ethanol, and subsequent drying via other means in order to meet the MFGE water specification. The distillation sequence generally involves separating solids and some water from the effluent stream of a fermentation process, such as through the use of a beer column or other suitable solids separation unit. The process stream from a solids separation unit, containing nominally from about 55% by weight to about 70% by weight ethanol is sent to a second distillation tower, also known as a rectifier column, to obtain an ethanol-water overhead product near the ethanol-water azeotropic mixture concentration.

Dehydration of the ethanol-water rectifier column overhead product can then be accomplished via pressure swing molecular sieve adsorption (PSA), or via other processes such as extractive distillation. The pressure swing molecular sieve adsorption (PSA) technology commonly used to dehydrate a rectifier column overhead product containing ethanol and water is an adiabatic process, which is the reason that distillation is normally used to minimize the water in the ethanol-water mixture that feeds the PSA unit.

A U.S. patent application filed Dec. 17, 2008, U.S. application Ser. No. 12/337,154, incorporated herein in its entirety, teaches the simultaneous separation of water from an ethanol-water mixture and heat pumping the heat in temperature controlled adsorption (TCA) feed water to a pressure (and temperature) level enabling useful process heat recovery. TCA technology enables greater than 99% ethanol recovery. Nevertheless, some ethanol loss to raffinate is inevitable in that design due to ethanol coadsorption and nonselective equipment void space. The adsorbent water concentration difference between the adsorption and regeneration steps is adsorbent water delta loading that is, water adsorption capacity. Adsorption and regeneration operating conditions determine to a great extent the TCA adsorbent water delta loading. The "residual" water loading, adsorbent water concentration at the end of the regeneration cycle is lessened by reducing the water partial pressure in contact with the TCA adsorbent. Water desorbed from the adsorbent during regeneration is removed via the TCA raffinate stream. The temperature at which the raffinate condenses determines its vapor pressure which in turn directly affects water partial pressure in contact with the adsorbent. As implied in U.S. application Ser. No.

12/337,154, the temperature at which water in the raffinate stream condenses is dependent on the heat sink temperature. For the single step regeneration process shown in that application, the heat sink selected for condensing raffinate from TCA regeneration impacts both adsorbent capacity, and heat recovery to the process via heat pumping. If a utility heat sink is used (e.g. cooling water), adsorbent capacity is maximized while TCA heat pump performance is lessened since heat from water in the raffinate is not recovered to the process; TCA heat pump performance is defined as (TCA heat delivered to the process)/(TCA regeneration heat input). If a process heat sink is used, TCA heat pump performance increases but adsorbent residual loading will depend on the process heat sink temperature. A TCA regeneration process that enables recovery of ethanol otherwise lost to the raffinate stream, and that decouples the adsorbent capacity and heat pump performance dependency is desirable.

It has now been found that a multi-step regeneration cycle enables an increase in the recovery of ethanol and provides significant operating flexibility to balance the trade-off between TCA heat pump performance and water adsorption capacity.

SUMMARY OF THE INVENTION

The systems and processes disclosed herein relate to utilizing heat pumping during the dehydration of process streams containing ethanol and water for producing motor fuel grade ethanol (MFGE).

The invention provides a process for dehydration of a process stream for the production of motor fuel grade ethanol that includes separating a fermentation beer stream in a solids separation unit to provide a bottoms stream including solids, and a process stream including ethanol and water. The process stream can be provided to a first temperature controlled adsorber that is undergoing adsorption. The first temperature controlled adsorber can have one or more adsorption flow passages containing an adsorptive material coating and one or more heat transfer flow passages. The process stream can be passed through the one or more adsorption flow passages, where water can be adsorbed by the adsorptive material coating to produce an MFGE product stream, and heat of adsorption can be generated in the one or more adsorption flow passages. A cooling fluid can be provided to the first temperature controlled adsorber, and heat of adsorption can be removed by passing a cooling fluid through the one or more heat transfer flow passages to produce a heated cooling fluid. The heat from the heated cooling fluid can be provided to a heat sink.

The process also includes providing a second temperature controlled adsorber undergoing regeneration that is isolated from the process stream. The second temperature controlled adsorber has one or more adsorption flow passages containing an adsorptive material coating and one or more heat transfer flow passages. A heating fluid is provided to the one or more heat transfer flow passages of the second temperature controlled adsorber, and the adsorptive material coating can be regenerated by removing water, producing a raffinate stream which contains water and residual ethanol that is removed from the second temperature controlled adsorber. The adsorbed water is desorbed at a thermal condition making possible useful heat recovery and flows from the adsorbent coated process passages via the raffinate stream. The multi-step regeneration cycle starts with all raffinate valves closed. After a short time period into the regeneration cycle and with raffinate sufficiently pressurized, the first raffinate valve opens directing raffinate flow to a location upstream of the TCA adsorption process. In this way raffinate that is relatively enriched in ethanol is recycled to the TCA adsorption step. As the regeneration process continues, the first raffinate valve closes and the second raffinate valve opens directing raffinate flow to the highest temperature level heat sink.

The raffinate condensation rate will decrease as regeneration progresses. Next, the second raffinate valve closes and the third raffinate valve opens directing raffinate flow to the next highest temperature level heat sink. Raffinate condensation continues until the multi-step regeneration cycle is completed by closing the third raffinate valve. The process described herein is a three step regeneration cycle. Additional regeneration cycle steps can be included as may be contemplated by one of skill in the art.

The cooled heating fluid can be used as the cooling fluid that is provided to the first temperature controlled adsorber.

Unless otherwise specified, the terms "stream" and "fluid" as used herein should be understood as encompassing either liquid or vapor, or both, as suitable based upon the temperature and pressure of the stream or fluid as suitable for the intended application.

BRIEF DESCRIPTION OF THE DRAWINGS

Specific examples have been chosen for purposes of illustration and description, and are shown in the accompanying drawings, forming a part of the specification.

FIG. 2a is a perspective view of a temperature controlled adsorber that can be used in the process of FIG. 1.

FIG. 2b is a close-up view of a portion of FIG. 2a.

FIG. 2c is a close-up view of another portion of FIG. 2a.

FIG. 2d is a close-up view showing the thickness of a separator plate.

FIG. 3 is a perspective view of a portion of a temperature controlled adsorber of FIG. 2a.

DETAILED DESCRIPTION

Figure 1:
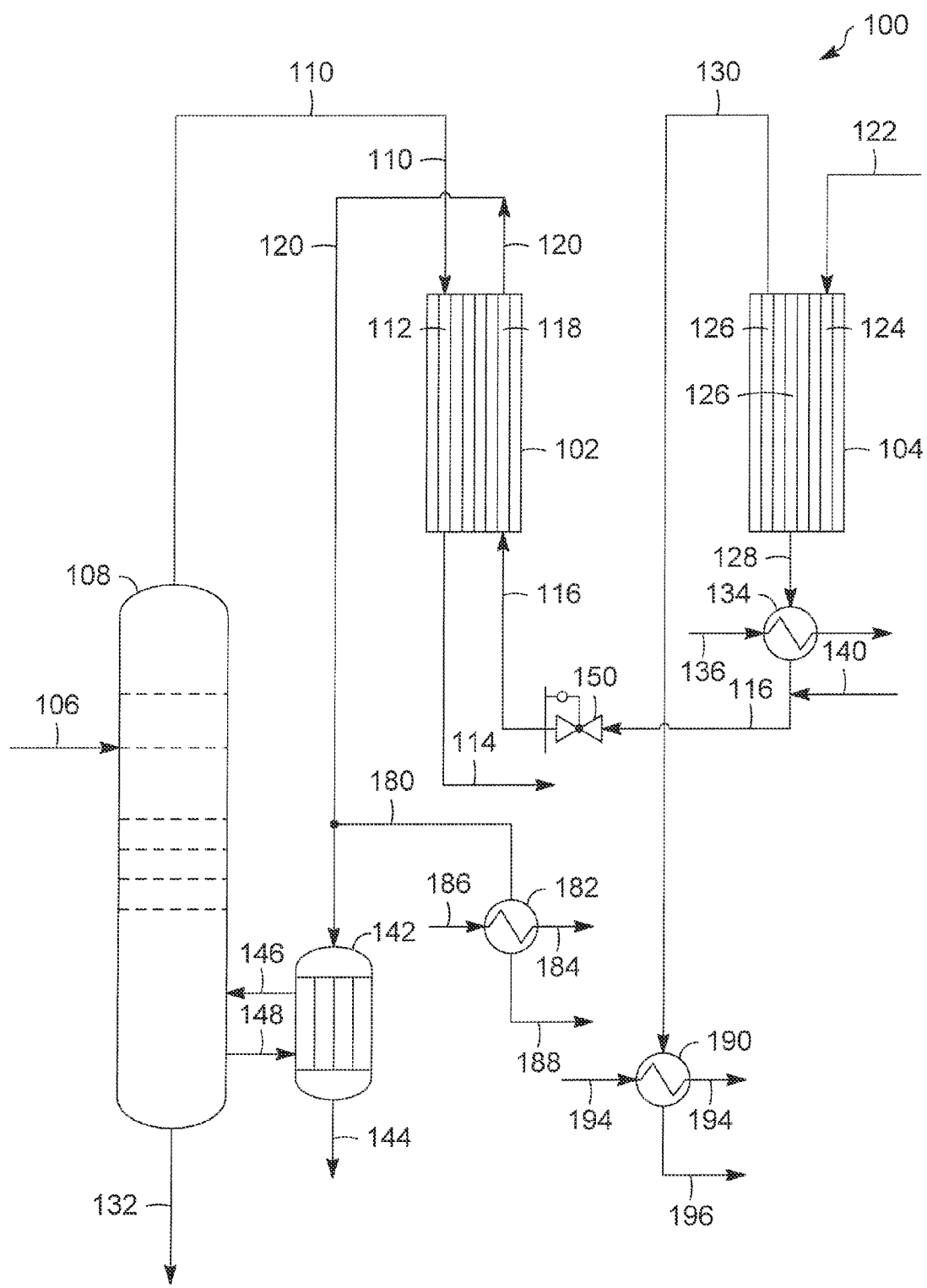
FIG. 1 illustrates a simplified process flow diagram for a processes for producing motor fuel grade ethanol (MFGE) utilizing temperature controlled adsorbers and heat pumping of the associated heat of water adsorption.

Systems and processes are disclosed herein relating to processes for dehydrating process streams containing ethanol and water for producing motor fuel grade ethanol (MFGE). The systems and processes disclosed herein can include heat pumping that can be utilized in conjunction with temperature controlled adsorption of water from such process streams. The systems and processes can preferably separate water from a process stream containing ethanol and water via temperature controlled adsorption, and heat pump the associated heat of water adsorption to a level enabling heat recovery within the process or other available heat sink. In at least some instances, the heat recovered via heat pumping can reduce the cost of MFGE production by reducing the process hot and cold utility requirements.

Some examples of systems and processes for temperature controlled adsorption in dehydrating water rich streams, including process streams for the production of MFGE, are disclosed in co-pending U.S. application Ser. No. 12/337,248 entitled "Temperature Controlled Adsorption For Dehydration Of Water Rich Streams," to David A. Wegerer and Stephen Robert Dunne, the content of which is hereby incorporated herein in its entirety.

Preferably, temperature controlled adsorption systems and processes can operate at conditions approaching isothermal conditions. In such examples, one or more benefits over operating an adiabatic adsorbent system or process can be achieved. For example, the upper limit on water concentration in the fluid to be treated can also be eliminated, providing the ability for dehydration of extremely water-rich streams. Additionally, increased differential loading potential can be provided, with substantially lower loadings achieved during regeneration and higher loadings achievable during adsorption steps. Lower product dew-points for water in the product stream, and smaller equipment size for a given duty can be also achieved. Other benefits can include reduction of purge gas requirements during the regeneration step and simultaneous increase of the potential for recovering high concentrations of adsorbate (i.e. water) in the regeneration gas. Flexibility in selecting the heating and cooling heat transfer media with minimal impact on desired process streams can also be provided. Further, extremely rapid thermal swing adsorption with cycle times at or below current adiabatic PSA separation processes can be achieved, which can result in smaller adsorber systems, which saves both capital and energy.

The multi-step regeneration cycle described herein enables increasing the recovery of ethanol, and provides operating flexibility to balance the trade-off between TCA heat pump performance and water adsorption capacity. The raffinate stream vapor pressure changes with time during the TCA regeneration cycle. The vapor pressure exceeds the TCA process feed pressure through a substantial portion of the cycle. Additionally, raffinate at the start of the regeneration step is relatively enriched in ethanol since equipment non-selective void space is occupied by a mixture of TCA feed and extract and co-adsorbed ethanol is preferentially desorbed at the beginning of the cycle. A multi-step regeneration cycle that recycles a select portion of the pressurized raffinate specifically, the portion relatively enriched in ethanol, to a location upstream of the TCA adsorption process will increase overall ethanol recovery.

A multi-step regeneration cycle and process scheme that incorporates different temperature level heat sinks makes it possible to decouple the adsorbent capacity and heat pump performance dependency. As mentioned previously, the raffinate stream vapor pressure changes during the TCA regeneration cycle. The dynamic vapor pressure behavior can be exploited for heat recovery by heat exchange with heat sinks available at dissimilar temperature levels. For example, the typical relationship between raffinate condensing temperature and adsorbent delta loading for a single step TCA regeneration cycle will result in 12.9 wt-% water adsorbent delta loading with raffinate condensing at 40° C. A cooling water utility heat sink is used in order to condense the raffinate at 40° C. Since none of the raffinate heat is recovered to the process, TCA (Heat Delivered to Process)/(Regeneration Heat Input)=1. Alternatively, consider a two step regeneration cycle in which raffinate heat is rejected to heat sinks at different temperature levels thereby improving TCA heat pump performance without sacrificing adsorbent delta loading. For example, a two step regeneration process that firstly rejects heat to a process heat sink capable of condensing raffinate at 86° C. and secondly rejects the remaining raffinate heat at 40° C. will result in about 12.9 wt-% water adsorbent delta loading. The heat recovered to the process during the first step results in improved heat pump performance; TCA (Heat Delivered to Process)/(Regeneration Heat Input)=1.37. The second step uses a cooling water utility heat sink in order to condense the raffinate at 40° C. In contrast to the single step regeneration cycle, the multi-step cycle improves heat pump performance by recovering some of the raffinate heat to the process without sacrificing adsorbent delta loading.

Figure 5:
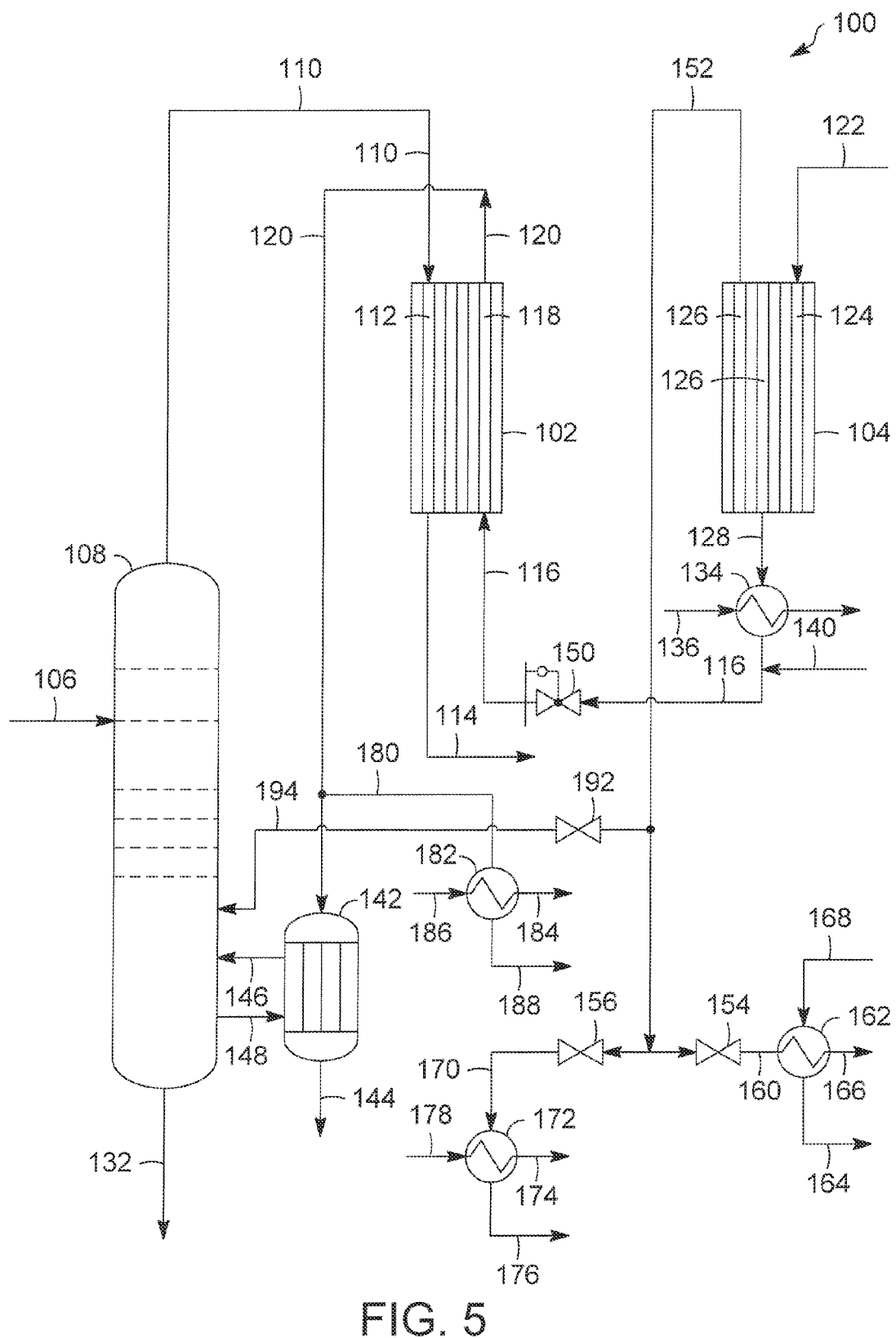
FIG. 5 is simplified process diagram that shows a multi-step regeneration cycle with multiple raffinate process heat sinks.

A multi-step regeneration cycle for a distillation-temperature controlled adsorption process is illustrated in FIG. 5. The multi-step cycle is made possible by including valves on the raffinate stream which direct raffinate flow to a location upstream of the TCA adsorption process, or to one of multiple heat sinks The valves are opened and closed sequentially, that is, raffinate flows through one valve at a time, except for a transition period during which one valve is closing and another is opening. The sequence is implemented via a process control system. Referring to FIG. 5, fermentation Beer is fed to a Beer column which separates solids and some water. The Beer column bottom product is a solids containing water stream. Ethanol is recovered in the Beer column overhead stream as an ethanol-water mixture. The Beer column overhead ethanol-water mixture flows to the TCA water removal and heat pumping process. The TCA apparatus will typically consist of multiple adsorbent coated plate-fin heat exchangers that cycle through alternating water adsorption and adsorbent regeneration steps. For the following discussion, TCA-A refers to the TCA in the water adsorption step and TCA-R refers to the TCA in the adsorbent regeneration step. During the adsorption step, slightly superheated ethanol-water vapor from the Beer column overhead flows through TCA-A's adsorbent coated process passages and exits substantially free of water via the extract stream.

Simultaneously, cooling fluid passes through TCA-A's heating/cooling side passages thereby removing the heat generated by the process-side water adsorption. Water vapor from TCA-A's heating/cooling passages flows to a Beer column reboiler, or alternatively, to another suitable process heat sink. In either case, vaporized TCA-A coolant is condensed against a process heat sink thereby recovering heat to the process. In this way, low level heat is pumped from the Beer column overhead stream and recovered as useable process heat. During the adsorbent regeneration step, TCA-R is isolated from the Beer column overhead ethanol-water mixture and regeneration steam is passed through TCA-R's heating/cooling side passages to provide the adsorbent regeneration heat requirement. The adsorbed water is desorbed at a thermal condition making possible useful heat recovery and flows from TCA-R's adsorbent coated process passages via the raffinate stream. The multi-step regeneration cycle starts with all raffinate valves closed. After a short time period into the regeneration cycle and with raffinate sufficiently pressurized, the first raffinate valve opens directing raffinate flow to a location upstream of the TCA adsorption process. In this way raffinate that is relatively enriched in ethanol is recycled to the TCA adsorption step. As the regeneration process continues, the first raffinate valve closes and the second raffinate valve opens directing raffinate flow to the highest temperature level heat sink. The raffinate condensation rate will decrease as regeneration progresses. Next, the second raffinate valve closes and the third raffinate valve opens directing raffinate flow to the next highest temperature level heat sink. Raffinate condensation continues until the multi-step regeneration cycle is completed by closing the third raffinate valve. This disclosure and FIG. 5 describe a three step regeneration cycle. The cycle could include more steps with the addition of raffinate flow diverter valves and suitable heat sinks.

FIG. 1 illustrates a process for the dehydration of a process stream 110 for use in producing motor fuel grade ethanol (MFGE), which utilizes temperature controlled adsorbers and also includes heat pumping of the associated heat of water adsorption. The MFGE production process is indicated generally at 100.

As shown in FIG. 1, the MFGE production process 100 includes a first temperature controlled adsorber 102, and a second temperature controlled adsorber 104. Temperature controlled adsorbers 102 and 104 are preferably adsorbent containing contactors having internal indirect heat transfer passages. Either or both of the temperature controlled adsorbers 102 and 104 as illustrated in FIG. 1 can be a temperature controlled adsorber of the type illustrated generally at 40 in FIGS. 2a-2d, 3 and 4.

As shown in FIG. 2a, temperature controlled adsorber 40 is a plate-fin type heat exchanger with one or more adsorption flow passages 53 and one or more heat transfer flow passages 55. The adsorption flow passages 53 contain an adsorptive material coating 46 that is applied by a wash-coating process. During the wash-coating process, the adsorption flow passages 53 are wash coated with a wash-coating fluid that contains an adsorbent material suitable for water adsorption including molecular sieves Type A and X, NaY, silica gel, alumina, and MOLSIV™ DDZ-70, which is produced by UOP. The wash-coating fluid also contains an organic polymer system and an organic solvent or carrier fluid. In one example, an adsorptive material coating 46 can contain a polymer and a zeolite, such as, for example, a Type 4A or a Type 3A zeolite.

A wash-coating process can comprise a step of heating a component to be coated, a step of contacting the surface of the component with a slurry comprising an adsorbent and a binder to form an adsorptive material coating 46, and a step of hardening the adsorptive material coating 46. For some applications, the step of contacting may comprise dipping the surface into the slurry or spraying the surface with the slurry.

The adsorptive material coating 46 may have an adsorptive coating thickness 77 (see FIG. 3) of between about 0.004 inches (0.010 cm) and about 0.052 inches (0.13 cm), preferably from about 0.014 inches (0.035 cm) to about 0.023 inches (0.058 cm). The adsorptive coating thickness 77 may be measured through the adsorptive material coating 46 and about perpendicular to the adsorption zone fin 58. The adsorptive coating thickness 77 may vary with application and may depend on factors including the dimensions of the adsorption zone fins 58, the desired dimensions of the adsorption flow passage 55 and the application. US 2008/0023181 A1, the disclosure of which is hereby incorporated by reference in its entirety, describes the rudiments of the wash-coating process and some of the benefits that ensue in sorption cooling systems.

As illustrated in FIGS. 2a-2d, adsorption heat exchanger 40 can comprise at least one adsorption layer 50, at least one heat transfer layer 51 and a separator plate 52 positioned between and in contact with the adsorption layer 50 and the heat transfer layer 51. The adsorption heat exchanger 40 can comprise a plurality of adsorption layers 50 and a plurality of heat transfer layers 51. The adsorption layers 50 and heat transfer layers 51 may be positioned in a stacked arrangement of alternating adsorption layers 50 and heat transfer layers 51. In other words, one adsorption layer 50 may be positioned between two heat transfer layers 51; and one heat transfer layer 51 may be positioned between two adsorption layers 50. The adsorption heat exchanger 40 can comprise a plurality of separator plates 52 positioned such that one separator plate 52 is between and in contact with each adsorption layer/heat transfer layer pair. In other words, the separator plate 52 may be positioned between the adsorption layer 50 and the heat transfer layer 51. As defined herein, an adsorption layer/heat transfer layer pair may comprise an adsorption layer 50 and a heat transfer layer 51 positioned adjacent to one another.

The adsorption layer 50 may provide an adsorption flow passage 53 through the adsorption heat exchanger 40. The adsorption flow passage 53 may be in a direction parallel to an adsorption flow line 54. The heat transfer layer 51 may define a heat transfer flow passage 55 through the adsorption heat exchanger 40. The heat transfer flow passage 55 may be in a direction parallel to a heat transfer flow line 56. The adsorption flow line 54 may be about 90° from the heat transfer flow line 56. This type of system provides cross flow heat exchange. In alternative examples, an adsorption heat exchanger can operate with either parallel or counter flow heat transfer.

Figure 3:
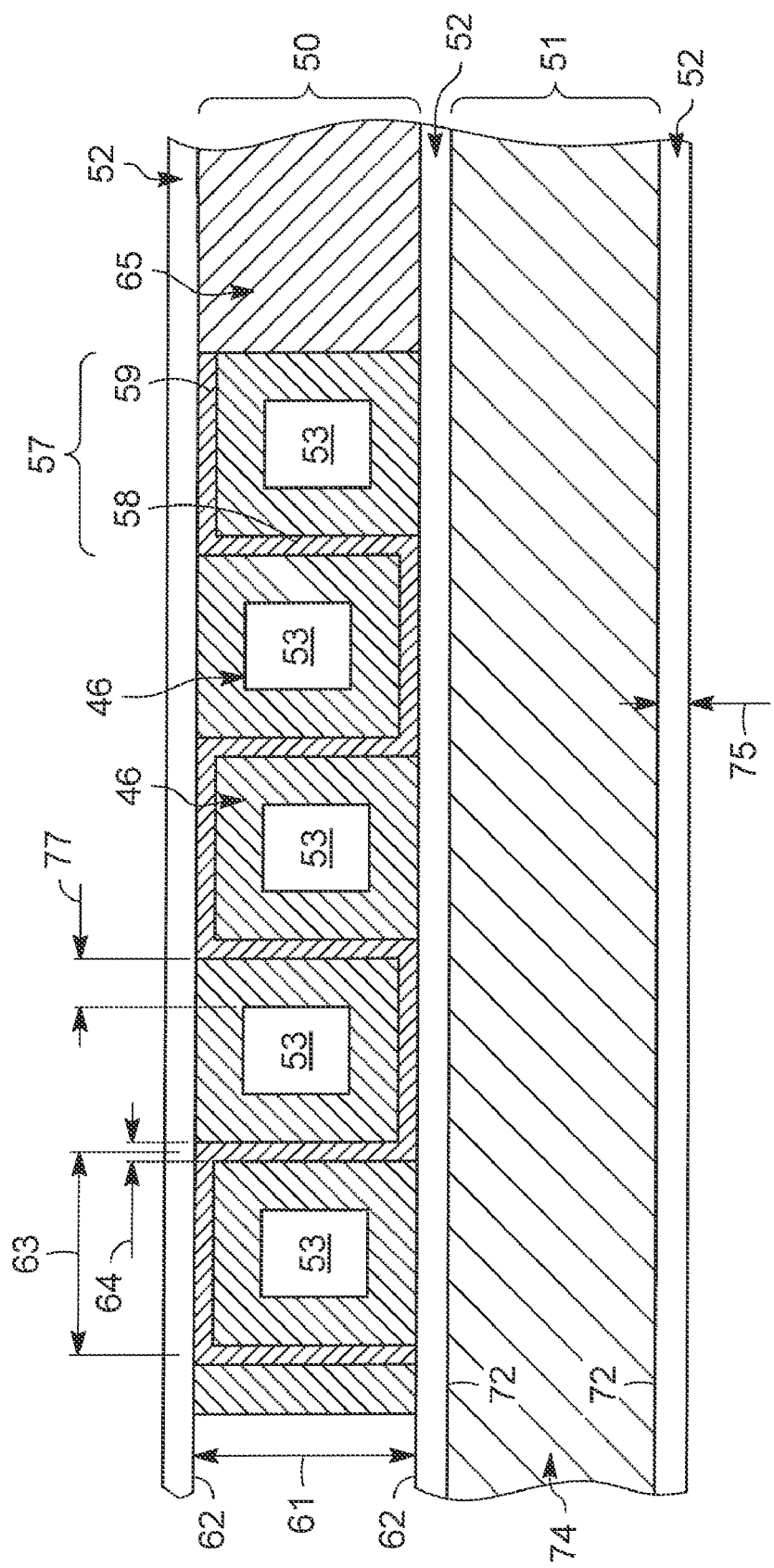

As depicted in FIG. 3, the adsorption layer 50 can include an adsorption zone corrugated sheet 57 and the adsorptive material coating 46. The adsorption zone corrugated sheet 57 may be in contact with and extend between two separator plates 52. The adsorption zone corrugated sheet 57 may comprise a plurality of adsorption zone fins 58 and a plurality of adsorption zone contact portions 59. The adsorption zone fin 58 may be the portion of the adsorption zone corrugated sheet 57 that is perpendicular to and extends between the separator plates 52. The adsorption zone contact portion 59 may be the portion of the adsorption zone corrugated sheet 57 that is parallel to and in contact with the separator plate 52.

The adsorption zone fins 58 may be positioned about perpendicular to the separator plates 52 and may extend about parallel to the adsorption flow line 54. The adsorption zone fins 58 may direct the flow of an adsorbate rich stream 60, as shown in FIG. 2a, through the adsorption heat exchanger 40 and may provide a support for at least a portion of the adsorptive material coating 46. The adsorption zone fin 58 may be in contact with and extend between two separator plates 52. The adsorption fin height 61 may vary with application and may depend on factors including the composition of the adsorption zone fin 58 and the application. The adsorption fin thickness 64 may vary with application and may depend on factors including the composition of the adsorptive material coating 46 and the application. The density of adsorption zone fins (fins/inch) may vary with application and may depend on factors including the thickness of the adsorptive material coating 46 and the desired volume of the adsorption flow passage 53. The density of the adsorption zone fins 58 may be defined as the number of fins per inch of adsorption layer width as measured perpendicular to the adsorption flow line 54 and parallel to the separator plate 52.

The adsorption zone contact portions 59 may be positioned about parallel to and in contact with the separator plates 52. The adsorption zone contact portions 59 may be brazed to an adsorption zone facing side 62 of the separator plates 52. The adsorption zone contact portions 59 may provide a support for at least a portion of the adsorptive material coating 46, as depicted in FIG. 3. In other words, one side of the adsorption zone contact portion 59 may be brazed to the separator plate 52 and the other side may be coated with the adsorptive material coating 46. The adsorption contact width 63 is not an independent parameter. Once the density of the adsorption zone fins 58 and the adsorption fin thickness 64 have been specified the adsorption contact width 63 is a determinate value. The adsorption contact portion width 63 may vary and may depend on the desired density of the adsorption zone fins 58. The adsorption contact portion width 63 may be inversely proportion to the density of the adsorption zone fins 58.

For some applications, in lieu of the adsorption zone corrugated sheet 57, the adsorption layer 50 may comprise a plurality of adsorption zone fins 58 brazed directly to the separator plates 52. The adsorption zone fins 58 of the adsorption layer 50 may increase the surface area available for adsorptive material coating 46, thereby enhancing the adsorption/desorption efficiency of the adsorption heat exchanger 40.

Adsorption layer 50 may include two adsorption zone header bars 65, as depicted in FIG. 2a. The adsorption zone header bars 65 may be positioned parallel to the adsorption flow line 54. One adsorption zone header bar 65 may be positioned at one side of the adsorption layer 50 and the other adsorption zone header bar 65 may be positioned at the opposing side of the adsorption layer 50. The adsorption zone header bars 65 may be brazed to the separator plates 52 and may provide structural support to the adsorption heat exchanger 40.

The adsorption zone corrugated sheet 57, the adsorption zone fin 58, the adsorption zone contact portion 59 and adsorption zone header bar 65 each may comprise a material, such as but not limited to, aluminized Mylar®, a polymer composite, or a metal. Mylar® is a polyester film produced by E.I. Du Pont De Nemours and Company. Useful metals may include aluminum, copper, titanium, brass, stainless steel, other light metals and alloys with high conductivity, and graphite fiber composite materials. Components of the adsorption layer 50 may provide support for the adsorptive material coating 46.

The adsorptive material coating 46 of the adsorption layer 50 may define the adsorption flow passage 53, as depicted in FIG. 3. For some embodiments of the present invention, the adsorptive material coating 46 may define at least a portion of the adsorption flow passage 53. The adsorptive material coating 46 may be positioned on and in contact with the adsorption zone fins 58. Additionally, the adsorptive material coating 46 may be positioned on and in contact with the adsorption zone contact portions 59. Further, the adsorptive material coating 46 may be positioned on and in contact with at least a portion of the adsorption zone facing side 62 of the separator plates 52, as depicted in FIG. 3.

Figure 4:
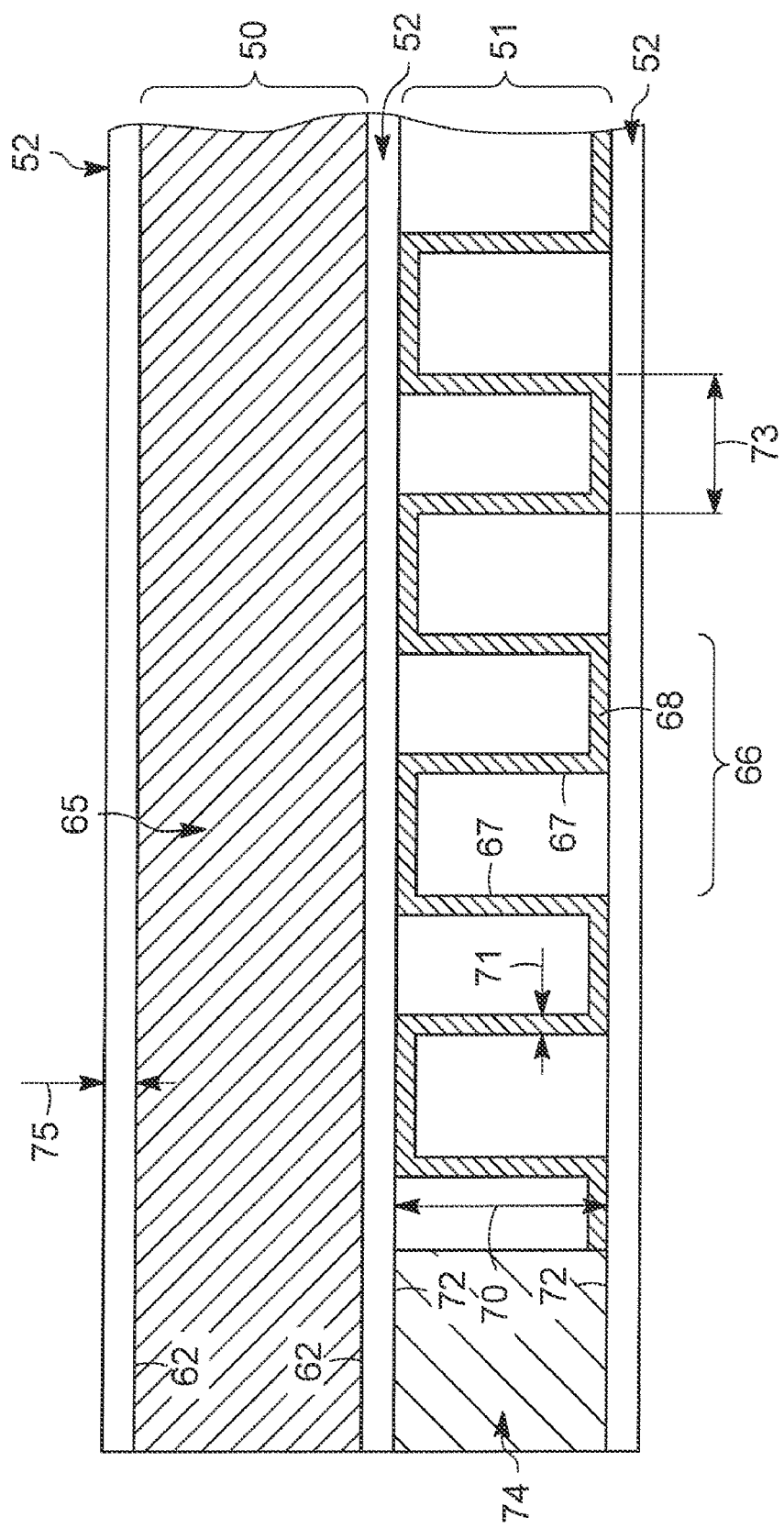
FIG. 4 is a rotated view of FIG. 3.

The heat transfer layer 51 may include a heat transfer zone corrugated sheet 66, as depicted in FIG. 4. The heat transfer zone corrugated sheet 66 may be in contact with and extend between two separator plates 52. The heat transfer zone corrugated sheet 66 may comprise a plurality of heat transfer zone fins 67 and a plurality of heat transfer zone contact portions 68. The heat transfer zone fin 67 may be the portion of the heat transfer zone corrugated sheet 66 that is perpendicular to and extends between the separator plates 52. The heat transfer zone contact portion 68 may be the portion of the heat transfer corrugated sheet 66 that is parallel to and in contact with the separator plate 52.

The heat transfer zone fins 67 may be positioned about perpendicular to the separator plates 52 and may extend about parallel to the heat transfer flow line 56. The heat transfer zone fins 67 may direct the flow of heat transfer fluid 69, as shown in FIG. 2a, through the adsorption heat exchanger 40. The heat transfer zone fins 67 may increase the heat transfer efficiency of the adsorption heat exchanger 40. The heat transfer zone fin 67 may be in contact with and extend between two separator plates 52. The heat transfer fin height 70 may vary with application and may depend on factors including the composition of the heat transfer zone fin 67 and the application. The heat transfer fin thickness 71 may vary with application and may depend on factors including the composition of the heat transfer fluid 69 and the application. The density of heat transfer zone fins (fins/inch) may vary with application and may depend on factors including the composition of the heat transfer fluid 69 and the desired volume of the heat transfer flow passage 55. The density of the heat transfer zone fins 67 may be defined as the number of fins per inch of the heat transfer layer width as measured perpendicular to the heat transfer flow line 56 and parallel to the separator plate 52.

The heat transfer zone contact portions 68 may be positioned about parallel to and in contact with the separator plates 52. The heat transfer zone contact portions 68 may be brazed to a heat transfer zone facing side 72 of the separator plates 52. The heat transfer contact portion width 73 may vary and may depend on the desired density of the heat transfer zone fins 67. The heat transfer contact portion width 73 may be inversely proportion to the density of the heat transfer zone fins 67.

For some applications, in lieu of the heat transfer zone corrugated sheet 66, the heat transfer layer 51 may comprise a plurality of heat transfer zone fins 67 brazed directly to the separator plates 52.

The heat transfer layer 51 may include two heat transfer zone header bars 74, as depicted in FIG. 2a. The heat transfer zone header bars 74 may be positioned parallel to the heat transfer flow line 56. One heat transfer zone header bar 74 may be positioned at one side of the heat transfer layer 51 and the other heat transfer zone header bar 74 may be positioned at the opposing side of the heat transfer layer 51. The heat transfer zone header bars 74 may be brazed to the separator plates 52 and may provide structural support to the adsorption heat exchanger 40.

The heat transfer zone corrugated sheet 66, the heat transfer zone fin 67, the heat transfer zone contact portion 68 and heat transfer zone header bar 74 each may comprise any suitable material, such as but not limited to, aluminized Mylar®, a polymer composite, or a metal. Useful metals may include aluminum, copper, titanium, brass, stainless steel, other light metals and alloys with high conductivity, and graphite fiber composite materials.

The separator plate 52 of the adsorption heat exchanger 40 may comprise a sheet material structure, as depicted in FIGS. 2a-c. The separator plate 52 may be positioned parallel to the layers 50 and 51, as shown in FIGS. 3 and 4. One separator plate 52 may be positioned between and in contact with each adsorption layer/heat transfer layer pair. The separator plate 52 may prevent the flow of adsorbate 60 from entering the heat transfer layer 51 and prevent the flow of heat transfer fluid 69 from entering the adsorption layer 50. The separator plate 52 may comprise any suitable material, such as but not limited to, aluminized Mylar®, a polymer composite, or a metal. Useful metals may include aluminum, copper, titanium, brass, stainless steel, other light metals and alloys with high conductivity, and graphite fiber composite materials. The width and length of the separator plate 52 may vary and may be about equal to the width and length of the layers 50 and 51.

The adsorption heat exchanger 40 further may comprise two side plates 76, as depicted in FIG. 2a. The side plates 76 may be positioned parallel to the layers 50 and 51. One side plate 76 may be positioned at one side of the adsorption heat exchanger 40 and the other side plate 76 may be positioned at the opposing side of the adsorption heat exchanger 40. The side plates 76 may comprise any suitable material, such as but not limited to, aluminized Mylar®, a polymer composite, or a metal. For some applications, the side plates 76 may be brazed to and provide structural support for the adsorption heat exchanger 40.

Referring back to FIG. 1, fermentation beer stream 106 of MFGE production process 100, which is an effluent stream from a process of fermentation of sugars that may be derived from starches and lignocellulose, is provided to a solids separation unit, such as beer column 108. Fermentation beer stream 106 is a water-rich mixture containing water, alcohols, soluble solids, and insoluble solids. The alcohol content of beer stream 106 can be primarily ethanol. Fermentation beer stream 106 can contain from about 70% by weight water to about 90% percent by weight water. Additionally, fermentation beer stream 106 can contain from about 3% by weight ethanol to about 20% by weight ethanol. As illustrated, beer column 108 produces an overhead stream, which is shown as process stream 110, and bottoms stream 132. Bottoms stream 132 contains primarily water and solids. Process stream 110 can contain from about 10% by weight water to about 85% by weight water. Process stream 110, or at least a portion of process stream 110, can be in a vapor phase. When the solids separation unit is a beer column, such as is illustrated in FIG. 1, 99% by weight or greater of the ethanol in the fermentation beer stream 106 can typically be recovered in process stream 110 as a dilute ethanol and water mixture. In some examples, process stream 110 can contain from about 55% by weight ethanol to about 70% by weight ethanol, and from about 25% by weight water to about 45% by weight water. Process stream 110 can have any suitable temperature and pressure. For example, process stream 110 can have a temperature of from about 70° to about 110° C. Additionally, process stream 110 can have a pressure of from about 30 to about 175 kPa.

A certain amount of heat input and heat removal are provided to the beer column 108 in order to recover the ethanol as an overhead product, and to provide reflux to enrich the process stream 110. One or more reboilers 142 can be utilized for this purpose.

Process stream 110 is shown being directed to first temperature controlled adsorber 102. When first temperature controlled adsorber is undergoing regeneration, process stream 110 can be directed to a temperature controlled adsorber that is undergoing an adsorption cycle (not shown). For the purposes of explaining the present invention, temperature controlled adsorber 102, also referred to as TCA-A, will be described as undergoing adsorption, while temperature controlled adsorber 104, also referred to as TCA-R, will be described as undergoing regeneration. It should be understood that during operation, the temperature controlled adsorbers 102 and 104 are preferably each cycled through alternating adsorption and regeneration steps. Accordingly, when first temperature controlled adsorber 102 is undergoing adsorption, second temperature controlled adsorber 104 is preferably undergoing regeneration. Similarly, when second temperature controlled adsorber 104 is undergoing adsorption, first temperature controlled adsorber 102 is preferably undergoing regeneration. It should also be understood that each temperature controlled adsorber has sufficient connections and feeds to function appropriately when undergoing either adsorption or regeneration, although only a portion of the actual connections to each temperature controlled adsorber are illustrated in FIG. 1.

When first temperature controlled adsorber 102 is undergoing adsorption, process stream 110 is provided to one or more inlets of first temperature controlled adsorber 102. Optionally, process stream 110 can pass through a vapor superheater (not shown) prior to being provided to the first temperature controlled adsorber 102. Process stream 110 flows through the one or more adsorption flow passages 112 of the first temperature controlled adsorber 102. Water is adsorbed by an adsorptive material coating in the one or more adsorption flow passages 112. In one example, the adsorptive material coating contains a polymer and a zeolite, such as, for example, a Type 4A or a Type 3A zeolite. The adsorption of the water generates heat, known as the heat of adsorption. The water adsorption process removes water from the process stream 110, and produces a MFGE product stream 114. MFGE product stream 114 can be less than 5% water by weight, preferably less than 2% water by weight, and more preferably less than 1% water by weight. Most preferably, MFGE product stream 114 contains from about 0.25% water by weight to about 1.25% water by weight. MFGE product stream 114 preferably contains greater than about 98% by weight ethanol. MFGE product stream can have any suitable temperature, and in one example has a temperature of about 99° C. MFGE product stream 114 exits first temperature controlled adsorber 102, and can then be utilized in its desired application.

The heat of adsorption of the water that is generated in first temperature controlled adsorber 102 is removed by indirect heat exchange with a cooling fluid 116. As described in further detail below, cooling fluid 116 is provided to the one or more heat transfer flow passages 118 of the first temperature controlled adsorber 102, and exits the first temperature controlled adsorber 102 as heated cooling fluid 120. Heated cooling fluid 120 has a temperature that is greater than the temperature of the process stream 110 as it exits a solids separation unit.

In the absence of heat recovery, the hot utility load for the process illustrated in FIG. 1 is the heat required by the beer column 108 in producing the process stream 110 and the heat required to regenerate the second temperature controlled adsorber 104. Additionally, the cold utility load is the cooling required to produce solids separation unit reflux and the cooling required to remove the heat of water adsorption from the first temperature controlled adsorber 102. Through appropriate selection of heating and cooling media, adsorption conditions in the temperature controlled adsorbers, and process flow arrangement, both the hot and cold utility loads of the process 100 can be reduced.

Heat flows naturally from a higher temperature to a lower temperature. A heat pump transfers heat from a low temperature heat source to a higher temperature level heat sink. In order to transfer heat in such a manner, external energy is added to drive the heat pump. In the process illustrated in FIG. 1, a heat pump can be used to transfer heat from the process stream 110, which acts as the heat source, to the beer column reboiler 142, which acts as the heat sink. The heat pumping can be accomplished by transferring the heat of adsorption generated by the water being adsorbed in the one or more adsorption flow passages 112 of the first temperature controlled adsorber 102 to cooling fluid 116 at a vapor pressure that is higher than the process stream 110, and is sufficient to be used as a heat input for the beer column 108. The heat used to drive the heat pump is the heat used to regenerate the adsorbent, that is, to desorb the adsorbed water. In such an example, the heat pump reduces the beer column hot utility load by an amount approximately equal to the heat of water adsorption cooling load and the cold utility load is reduced by an amount approximately equal to the heat delivered to the Beer column.

As illustrated in FIG. 1, when first temperature controlled adsorber 102 is undergoing adsorption, second temperature controlled adsorber 104 undergoes regeneration. During regeneration, second temperature controlled adsorber 104 is isolated from process stream 110. A heating fluid 122 is provided to and passes through the one or more heat transfer flow passages 124 of the second temperature controlled adsorber 104. Heating fluid 122 can be water vapor at a temperature of from about 150° to about 250° C., for example at about 185° C. The heating fluid 122 provides heat via indirect heat exchange to the one or more adsorption flow passages 126 of the second temperature controlled adsorber 104. The heat provided by heating fluid 122 is preferably sufficient to provide the regeneration heat requirement for the one or more adsorption flow passages 126. Additionally, the pressure in the one or more adsorption flow passages 126 may be reduced to facilitate regeneration. Water that was adsorbed by the adsorptive material coating in the one or more adsorption flow passages 126 during the previous adsorption cycle of the second temperature controlled adsorber 104 is removed from the adsorptive material coating, and exits the second temperature controlled adsorber 104 as water effluent stream 130. Water effluent stream 130 is shown being sent to heat sink 190 with water condensation stream 196 exiting. Heat sink stream 194 is sent through heat sink 190 to provide desired transfer of heat.

As heating fluid 122 passes through the one or more heat transfer flow passages 124, it loses heat and exits the second temperature controlled adsorber 104 as cooled heating fluid 128. Cooled heating fluid 128 can be a condensate, containing at least some liquid water and some water vapor, and can have a temperature of from about 150° to about 250° C., for example at about 185° C.

Optionally, cooled heating fluid 128 can undergo subcooling to produce cooling fluid 116. During subcooling, the cooled heating fluid passes through heat exchanger 134, where the temperature of cooled heating fluid 128 is reduced by subcooling stream 136. Coolant stream 140 can also be added to cooled heating fluid 128 to further reduce the temperature of the fluid and produce cooling fluid 116. Cooling fluid 116 can have a temperature of from about 95° to about 130° C., for example about 100° C. Cooling fluid 116 can be passed to a pressure reducing device 150, where the pressure of cooling fluid 116 can be reduced to from about 75 to about 1080 kPa, for example about 105 kPa.

Cooling fluid 116 is provided to the one or more heat transfer flow passages 118 of the first temperature controlled adsorber 102. As it passes through the one or more heat transfer flow passages 118, cooling fluid 116 removes the heat of adsorption of the water that is generated during adsorption, and exits the first temperature controlled adsorber 102 as heated cooling fluid 120. Generally, the heat of adsorption provides sufficient heat to cooling fluid 116 to vaporize any liquid water within cooling fluid 116, and heated cooling fluid 120 is therefore in a vapor state. Heated cooling fluid 120 can have a temperature from about 95° to about 130° C., for example about 100° C.

Heat from the heated cooling fluid 120 can be provided to any suitable heat sink, including but not limited to, the solids separation unit illustrated as beer column 108. For example, heated cooling fluid 120 can be injected into the beer column 108, preferably near the bottom of beer column 108. Alternatively, heated cooling fluid 120 can be provided to a reboiler 142. In reboiler 142, the heated cooling fluid can be condensed, and the heat released from the heated cooling fluid 120 can be provided to the beer column 108 by reboiler return stream 146. Reboiler supply stream 148, at a temperature of about 80° to about 120° C., for example about 86° C. can be provided to the reboiler 142 from the beer column 108. Condensing of the heated cooling fluid 120 in reboiler 142 produces condensate stream 144.

Alternatively, a portion 180 of heated cooling fluid 120 is shown being sent to heat sink 182. Condensing of this portion 180 produces condensation stream 188 with a heat sink stream 186 that is shown passing to this heat sink 182 that recovers heat from the heated cooling fluid 120 and exiting heat sink 182 as stream 184 available with its heat for use within the system as needed.

FIG. 5 shows the multiple-step regeneration process of the present invention. Fermentation beer stream 106 of MFGE production process 100, which is an effluent stream from a process of fermentation of sugars that may be derived from starches and lignocellulose, is provided to a solids separation unit, such as beer column 108. Fermentation beer stream 106 is a water-rich mixture containing water, alcohols, soluble solids, and insoluble solids. The alcohol content of beer stream 106 can be primarily ethanol. Fermentation beer stream 106 can contain from about 70% by weight water to about 90% percent by weight water. Additionally, fermentation beer stream 106 can contain from about 3% by weight ethanol to about 20% by weight ethanol. As illustrated, beer column 108 produces an overhead stream, which is shown as process stream 110, and bottoms stream 132. Bottoms stream 132 contains primarily water and solids. Process stream 110 can contain from about 10% by weight water to about 85% by weight water. Process stream 110, or at least a portion of process stream 110, can be in a vapor phase. When the solids separation unit is a beer column, such as is illustrated in FIG. 5, 99% by weight or greater of the ethanol in the fermentation beer stream 106 can typically be recovered in process stream 110 as a dilute ethanol and water mixture. In some examples, process stream 110 can contain from about 55% by weight ethanol to about 70% by weight ethanol, and from about 25% by weight water to about 45% by weight water. Process stream 110 can have any suitable temperature and pressure. For example, process stream 110 can have a temperature of from about 70° to about 110° C. Additionally, process stream 110 can have a pressure of from about 30 to about 175 kPa.

A certain amount of heat input and heat removal are provided to the beer column 108 in order to recover the ethanol as an overhead product, and to provide reflux to enrich the process stream 110. One or more reboilers 142 can be utilized for this purpose.

Process stream 110 is shown being directed to first temperature controlled adsorber 102. When first temperature controlled adsorber is undergoing regeneration, process stream 110 can be directed to a temperature controlled adsorber that is undergoing an adsorption cycle (not shown). For the purposes of explaining the present invention, temperature controlled adsorber 102, also referred to as TCA-A, will be described as undergoing adsorption, while temperature controlled adsorber 104, also referred to as TCA-R, will be described as undergoing regeneration. It should be understood that during operation, the temperature controlled adsorbers 102 and 104 are preferably each cycled through alternating adsorption and regeneration steps. Accordingly, when first temperature controlled adsorber 102 is undergoing adsorption, second temperature controlled adsorber 104 is preferably undergoing regeneration. Similarly, when second temperature controlled adsorber 104 is undergoing adsorption, first temperature controlled adsorber 102 is preferably undergoing regeneration. It should also be understood that each temperature controlled adsorber has sufficient connections and feeds to function appropriately when undergoing either adsorption or regeneration, although only a portion of the actual connections to each temperature controlled adsorber are illustrated in FIG. 5.

When first temperature controlled adsorber 102 is undergoing adsorption, process stream 110 is provided to one or more inlets of first temperature controlled adsorber 102. Optionally, process stream 110 can pass through a vapor superheater (not shown) prior to being provided to the first temperature controlled adsorber 102. Process stream 110 flows through the one or more adsorption flow passages 112 of the first temperature controlled adsorber 102. Water is adsorbed by an adsorptive material coating in the one or more adsorption flow passages 112. In one example, the adsorptive material coating contains a polymer and a zeolite, such as, for example, a Type 4A or a Type 3A zeolite. The adsorption of the water generates heat, known as the heat of adsorption. The water adsorption process removes water from the process stream 110, and produces a MFGE product stream 114. MFGE product stream 114 can be less than 5% water by weight, preferably less than 2% water by weight, and more preferably less than 1% water by weight. Most preferably, MFGE product stream 114 contains from about 0.25% water by weight to about 1.25% water by weight. MFGE product stream 114 preferably contains greater than about 98% by weight ethanol. MFGE product stream can have any suitable temperature, and in one example has a temperature of about 99° C. MFGE product stream 114 exits first temperature controlled adsorber 102, and can then be utilized in its desired application.

The heat of adsorption of the water that is generated in first temperature controlled adsorber 102 is removed by indirect heat exchange with a cooling fluid 116. As described in further detail below, cooling fluid 116 is provided to the one or more heat transfer flow passages 118 of the first temperature controlled adsorber 102, and exits the first temperature controlled adsorber 102 as heated cooling fluid 120. Heated cooling fluid 120 has a temperature that is greater than the temperature of the process stream 110 as it exits a solids separation unit.

In the absence of heat recovery, the hot utility load for the process illustrated in FIG. 5 is the heat required by the beer column 108 in producing the process stream 110 and the heat required to regenerate the second temperature controlled adsorber 104. Additionally, the cold utility load is the cooling required to produce solids separation unit reflux and the cooling required to remove the heat of water adsorption from the first temperature controlled adsorber 102. Through appropriate selection of heating and cooling media, adsorption conditions in the temperature controlled adsorbers, and process flow arrangement, both the hot and cold utility loads of the process 100 can be reduced.

Heat flows naturally from a higher temperature to a lower temperature. A heat pump transfers heat from a low temperature heat source to a higher temperature level heat sink. In order to transfer heat in such a manner, external energy is added to drive the heat pump. In the process illustrated in FIG. 5, a heat pump can be used to transfer heat from the process stream 110, which acts as the heat source, to the beer column reboiler 142, which acts as the heat sink. The heat pumping can be accomplished by transferring the heat of adsorption generated by the water being adsorbed in the one or more adsorption flow passages 112 of the first temperature controlled adsorber 102 to cooling fluid 116 at a vapor pressure that is higher than the process stream 110, and is sufficient to be used as a heat input for the beer column 108. The heat used to drive the heat pump is the heat used to regenerate the adsorbent, that is, to desorb the adsorbed water. In such an example, the heat pump reduces the beer column hot utility load by an amount approximately equal to the heat of water adsorption cooling load and the cold utility load is reduced by an amount approximately equal to the heat delivered to the Beer column.

As illustrated in FIG. 5, when first temperature controlled adsorber 102 is undergoing adsorption, second temperature controlled adsorber 104 undergoes regeneration. During regeneration, second temperature controlled adsorber 104 is isolated from process stream 110. A heating fluid 122 is provided to and passes through the one or more heat transfer flow passages 124 of the second temperature controlled adsorber 104. Heating fluid 122 can be water vapor at a temperature of from about 150° to about 250° C., for example at about 185° C. The heating fluid 122 provides heat via indirect heat exchange to the one or more adsorption flow passages 126 of the second temperature controlled adsorber 104. The heat provided by heating fluid 122 is preferably sufficient to provide the regeneration heat requirement for the one or more adsorption flow passages 126. Additionally, the pressure in the one or more adsorption flow passages 126 may be reduced to facilitate regeneration. Water that was adsorbed by the adsorptive material coating in the one or more adsorption flow passages 126 during the previous adsorption cycle of the second temperature controlled adsorber 104 is removed from the adsorptive material coating, and exits the second temperature controlled adsorber 104 as water effluent stream 130. Water effluent stream 152 is shown exiting second controlled adsorber 102 and then undergoing a staged recovery of heat from this stream. There is shown in FIG. 5 a three part TCA regeneration system, including a two part heat recovery system, but if desired, there may be three or more heat recovery parts added to the system for improved recovery of the heat. Water effluent stream 152 is sent to raffinate valve 192, or raffinate valve 154 or raffinate valve 156. During operation, water effluent stream 152 is first sent to the Beer column through line 194 by opening valve 192 in order to recover ethanol that is coadsorbed with water or trapped in the nonselective equipment void space. Following the ethanol recovery step, valve 192 is closed and water effluent stream 152 is sent to the highest temperature heat sink, which is heat sink 172 in this FIG. 5 by opening of raffinate valve 156. The water effluent is sent through line 170 to heat sink 172 with water condensation stream 176 exiting after the water effluent stream passes through heat sink 170 with heat recovered into process stream 178 which is shown after passing through the heat sink 170 as process stream 174. As the regeneration process continues, raffinate valve 156 is closed and raffinate valve 154 is opened, allowing water effluent stream 152 to continue to line 160 to heat sink 162 with condensate 166 exiting and heat recovered from the water effluent stream passing into process stream 168 which exits heat sink 162 as process stream 164.

As heating fluid 122 passes through the one or more heat transfer flow passages 124, it loses heat and exits the second temperature controlled adsorber 104 as cooled heating fluid 128. Cooled heating fluid 128 can be a condensate, containing at least some liquid water and some water vapor, and can have a temperature of from about 150° to about 250° C., for example at about 185° C.

Optionally, cooled heating fluid 128 can undergo subcooling to produce cooling fluid 116. During subcooling, the cooled heating fluid passes through heat exchanger 134, where the temperature of cooled heating fluid 128 is reduced by subcooling stream 136. Coolant stream 140 can also be added to cooled heating fluid 128 to further reduce the temperature of the fluid and produce cooling fluid 116. Cooling fluid 116 can have a temperature of from about 95° to about 130° C., for example about 100° C. Cooling fluid 116 can be passed to a pressure reducing device 150, where the pressure of cooling fluid 116 can be reduced to from about 75 to about 1080 kPa, for example about 105 kPa.

Cooling fluid 116 is provided to the one or more heat transfer flow passages 118 of the first temperature controlled adsorber 102. As it passes through the one or more heat transfer flow passages 118, cooling fluid 116 removes the heat of adsorption of the water that is generated during adsorption, and exits the first temperature controlled adsorber 102 as heated cooling fluid 120. Generally, the heat of adsorption provides sufficient heat to cooling fluid 116 to vaporize any liquid water within cooling fluid 116, and heated cooling fluid 120 is therefore in a vapor state. Heated cooling fluid 120 can have a temperature from about 95° to about 130° C., for example about 100° C.

Heat from the heated cooling fluid 120 can be provided to any suitable heat sink, including but not limited to, the solids separation unit illustrated as beer column 108. For example, heated cooling fluid 120 can be injected into the beer column 108, preferably near the bottom of beer column 108. Alternatively, heated cooling fluid 120 can be provided to a reboiler 142. In reboiler 142, the heated cooling fluid can be condensed, and the heat released from the heated cooling fluid 120 can be provided to the beer column 108 by reboiler return stream 146. Reboiler supply stream 148, at a temperature of about 80° to about 120° C., for example about 86° C. can be provided to the reboiler 142 from the beer column 108. Condensing of the heated cooling fluid 120 in reboiler 142 produces condensate stream 144.

Alternatively, a portion 180 of heated cooling fluid 120 is shown being sent to heat sink 182. Condensing of this portion 180 produces condensation stream 188 with a heat sink stream 186 that is shown passing to this heat sink 182 that recovers heat from the heated cooling fluid 120 and exiting heat sink 182 as stream 184 available with its heat for use within the system as needed.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

The invention claimed is:

1. A process for dehydration of a process stream for the production of motor fuel grade ethanol, the process comprising:
    sending a fermentation beer stream to a solids separation unit;
    separating the fermentation beer stream in said solids separation unit to provide a bottoms stream including solids, and a process stream including ethanol and water;
    providing the process stream to a first temperature controlled adsorber that is undergoing adsorption, where the first temperature controlled adsorber has one or more adsorption flow passages containing an adsorptive material coating and one or more heat transfer flow passages;
    passing the process stream through the one or more adsorption flow passages, where water is adsorbed by the adsorptive material coating to produce a motor fuel grade ethanol product stream;
    providing a second temperature controlled adsorber that is isolated from the process stream and is undergoing regeneration, where the second temperature controlled adsorber has one or more adsorption flow passages containing an adsorptive material coating and one or more heat transfer flow passages;
    providing a heating fluid to the one or more heat transfer flow passages of the second temperature controlled adsorber;
    regenerating the adsorptive material coating by sending a heating stream through said heat transfer flow passages to remove water to produce a raffinate stream comprising water and ethanol; and then in turn
    sending the raffinate stream to a first heat sink at a higher temperature than a second heat sink and then to said second heat sink until said adsorption flow passages within said second temperature controlled adsorber are regenerated and said second temperature adsorber then undergoes adsorption.

2. The process of claim 1, wherein at least one of the first temperature controlled adsorber or the second temperature controlled adsorber is a plate-fin type heat exchanger.

3. The process of claim 1, wherein the process stream contains from about 5% by weight water to about 85% by weight water.

4. The process of claim 1, wherein the MFGE product contains less than about 5% by weight water.

5. The process of claim 1, wherein the raffinate stream is injected into the solids separation unit prior to said raffinate stream being sent to said first heat sink.

6. The process of claim 1, wherein the raffinate stream is provided to a reboiler that provides heat to the solids separation unit prior to said raffinate stream being sent to said first heat sink.

7. The process of claim 1, wherein the heating fluid is water vapor at a temperature of from about 150° to about 250° C.

8. The process of claim 1, wherein the raffinate stream is in a vapor phase.

9. The process of claim 1 further comprising:
    generating heat of adsorption in the one or more adsorption flow passages of the first temperature controlled adsorber;
    providing a cooling fluid to the first temperature controlled adsorber;
    removing heat of adsorption by passing the cooling fluid through the one or more heat transfer flow passages to produce a heated cooling fluid; and
    providing heat from the heated cooling fluid to a heat sink.

10. The process of claim 9 further comprising:
    producing a cooled heating fluid during regenerating of the adsorptive material coating; and
    using the cooled heating fluid as the cooling fluid that is provided to the first temperature controlled adsorber.

11. A process for dehydration of a process stream for the production of motor fuel grade ethanol, the process comprising:
    separating a fermentation beer stream that was produced in a beer column wherein said separation takes place in a solids separation unit to provide a bottoms stream including solids, and a process stream including ethanol and water;
    providing the process stream to a first temperature controlled adsorber that is undergoing adsorption, where the first temperature controlled adsorber has one or more adsorption flow passages containing an adsorptive material coating and one or more heat transfer flow passages;
    passing the process stream through the one or more adsorption flow passages, where water is adsorbed by the adsorptive material coating to produce an MFGE product stream;
    generating heat of adsorption in the one or more adsorption flow passages of the first temperature controlled adsorber;
    removing heat of adsorption by passing a cooling fluid through the one or more heat transfer flow passages to produce a heated cooling fluid;

providing heat from the heated cooling fluid to a first heat sink;

providing a second temperature controlled adsorber that is isolated from the process stream and is undergoing regeneration, where the second temperature controlled adsorber has one or more adsorption flow passages containing an adsorptive material coating and one or more heat transfer flow passages;

providing a heating fluid to the one or more heat transfer flow passages of the second temperature controlled adsorber;

regenerating the adsorptive material coating by removing water to produce a regeneration effluent stream; and providing heat from the regeneration effluent stream to a second heat sink and then to a third heat sink.

12. The process of claim 11, the process further comprising:

producing a cooled heating fluid during regenerating of the adsorptive material coating; and using the cooled heating fluid as the cooling fluid that is provided to the first temperature controlled adsorber.

13. The process of claim 11, wherein at least one of the first temperature controlled adsorber or the second temperature controlled adsorber is a plate-fin type heat exchanger.

14. The process of claim 11, wherein the process stream contains from about 10% by weight water to about 85% by weight water.

15. The process of claim 11, wherein the MFGE product contains less than about 5% by weight water.

16. The process of claim 11, wherein at least one of the first heat sink or the second heat sink is the solids separation unit.

17. The process of claim 16, wherein the regeneration effluent stream is injected into the solids separation unit or is provided to a reboiler that provides heat to the solids separation unit.

18. The process of claim 16, wherein the heated cooling fluid is injected into the solids separation unit or is provided to a reboiler that provides heat to the solids separation unit.

19. The process of claim 11, wherein the heating fluid 122 is water vapor at a temperature of from about 150° to about 250° C.

20. The process of claim 11, wherein the regeneration effluent stream is in a vapor phase.

* * * * *